United States Patent
Garnavi et al.

(10) Patent No.: US 10,762,459 B2
(45) Date of Patent: Sep. 1, 2020

(54) RISK DETECTION AND PEER CORRECTIVE ASSISTANCE FOR RISK MITIGATION WITHIN A WORK ENVIRONMENT

(71) Applicant: INTERNATIONAL BUSINESS MACHINES CORPORATION, Armonk, NY (US)

(72) Inventors: Rahil Garnavi, Macleod (AU); James R. Kozloski, New Fairfield, CT (US); Timothy Lynar, Alfred St. Kew (AU); John Wagner, Melbourne (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 729 days.

(21) Appl. No.: 14/984,417

(22) Filed: Dec. 30, 2015

(65) Prior Publication Data

US 2017/0193623 A1 Jul. 6, 2017

(51) Int. Cl.
*G06Q 10/06* (2012.01)
*G06Q 50/26* (2012.01)
(Continued)

(52) U.S. Cl.
CPC ........ *G06Q 10/0635* (2013.01); *G06N 5/045* (2013.01); *G06Q 50/01* (2013.01);
(Continued)

(58) Field of Classification Search
CPC ......... A62B 9/006; A42B 3/046; G06F 19/34; G06F 19/3418; G06Q 50/265; G06Q 50/26
(Continued)

(56) References Cited

U.S. PATENT DOCUMENTS 6,727,818 B1 * 4/2004 Wildman ............ G06F 19/3418
340/573.1
8,253,792 B2 8/2012 Wells et al.
(Continued)

FOREIGN PATENT DOCUMENTS

AU 2013101502 12/2013
AU 2014100282 4/2014
CN 101702258 3/2011

OTHER PUBLICATIONS

Disclosed Anonymously, System and Method for Ubiquitous Factory (UFACTORY) Safety Platform Using Location Awareness and Sensor Technologies, IP.com No. 000209545, IP.com Electronic Publication: Aug. 9, 2011.
(Continued)

*Primary Examiner* — Christine M Behncke
*Assistant Examiner* — Shelby A Turner
(74) *Attorney, Agent, or Firm* — Tutunjian & Bitetto, P.C.; Anthony Curro (57) ABSTRACT

Methods and systems for predicting injury risk include generating state sequences that precede a hazard event based on information regarding a user's state. A cognitive suite of workplace hygiene and injury predictors (WHIP) is generated based on the state sequences using a processor. The cognitive WHIP predicts a degree of risk correlated with each particular user state sequence. An advantageous relationship between the user and one or more socially connected users is determined. An ameliorative action is triggered when a user enters a high-risk state based on the advantageous relationship to the one or more connected users and proximity of the user to one or more other users.

20 Claims, 6 Drawing Sheets

(51) Int. Cl.
*G06Q 50/00* (2012.01)
*G06N 5/04* (2006.01)
*A61B 5/00* (2006.01)
*G06F 1/16* (2006.01)
*G05B 19/406* (2006.01)

(52) U.S. Cl.
CPC ............ *G06Q 50/265* (2013.01); *A61B 5/681* (2013.01); *A61B 5/7275* (2013.01); *G05B 19/406* (2013.01); *G06F 1/163* (2013.01)

(58) Field of Classification Search
USPC ..................................... 348/82–91, 143, 115
See application file for complete search history.

(56) References Cited

U.S. PATENT DOCUMENTS

| | | | | |
|---|---|---|---|---|
| 2006/0202819 | A1* | 9/2006 | Adamczyk | G08B 25/005 340/539.18 |
| 2008/0294016 | A1* | 11/2008 | Gobeyn | A61B 5/103 600/301 |
| 2010/0253526 | A1* | 10/2010 | Szczerba | G08B 21/06 340/576 |
| 2011/0054689 | A1* | 3/2011 | Nielsen | G05D 1/0088 700/258 |
| 2011/0105925 | A1* | 5/2011 | Hatakeyama | B60K 28/06 600/509 |
| 2011/0133927 | A1* | 6/2011 | Humphrey | A62B 99/00 340/539.11 |
| 2011/0184250 | A1* | 7/2011 | Schmidt | G06Q 10/00 600/300 |
| 2011/0259258 | A1* | 10/2011 | DePiero | G01D 21/00 116/200 |
| 2012/0010488 | A1* | 1/2012 | Henry | A61B 5/1118 600/365 |
| 2012/0203464 | A1* | 8/2012 | Mollicone | G06Q 10/0639 702/19 |
| 2013/0013331 | A1* | 1/2013 | Horseman | A61B 5/0022 705/2 |
| 2013/0053990 | A1* | 2/2013 | Ackland | G06Q 50/22 700/91 |
| 2013/0278414 | A1* | 10/2013 | Sprigg | G06F 19/3418 340/539.12 |
| 2014/0081179 | A1* | 3/2014 | Moore-Ede | A61B 5/1118 600/595 |
| 2014/0121550 | A1 | 5/2014 | McNair | |
| 2014/0156084 | A1* | 6/2014 | Rahman | G06F 1/1694 700/276 |
| 2014/0368601 | A1* | 12/2014 | deCharms | H04L 65/403 348/14.02 |
| 2015/0106020 | A1* | 4/2015 | Chung | G16H 40/67 702/19 |
| 2015/0182843 | A1 | 7/2015 | Esposito et al. | |
| 2015/0294595 | A1* | 10/2015 | Hu | G06Q 10/101 434/127 |
| 2016/0106174 | A1* | 4/2016 | Chung | A42B 3/0453 340/539.13 |
| 2016/0163186 | A1* | 6/2016 | Davidson | G08B 29/04 340/506 |
| 2016/0358500 | A1* | 12/2016 | Schlueter | G09B 5/02 |
| 2017/0017927 | A1* | 1/2017 | Domnick | G06Q 10/1091 |
| 2017/0038762 | A1* | 2/2017 | Canedo | B25J 9/1674 |
| 2017/0083679 | A1* | 3/2017 | Feder | G16H 50/30 |
| 2017/0127257 | A1* | 5/2017 | Saxena | H04W 4/60 |
| 2017/0154394 | A1* | 6/2017 | Kan | G06Q 50/28 |
| 2018/0122219 | A1* | 5/2018 | Caterino | H04L 63/0853 |

OTHER PUBLICATIONS

Disclosed Anonymously, Method and System for Alerting a Caregiver of Wakefulness and Activity of a Charge, IP.com No. 000233606, IP.com Electronic Publication: Dec. 18, 2013.
Paoli, et al., Expert Systems with Applications, Expert Systems with Applications, 39 (2012) 5566-5575.

* cited by examiner

RISK DETECTION AND PEER CORRECTIVE ASSISTANCE FOR RISK MITIGATION WITHIN A WORK ENVIRONMENT

BACKGROUND

Technical Field

The present invention relates to predicting dangerous conditions and, more particularly, to providing cognitive workplace hygiene and injury predictors to guide safety decisions.

Description of the Related Art

There are about 350,000 annual workplace fatalities and 270 million annual workplace injuries worldwide. In the United States alone, this results in about $750 billion in lost wages and productivity, medical expenses, administrative costs, motor vehicle damage, employers' uninsured costs, and fire loss. These numbers include about 4,400 worker deaths due to job injuries, close to 50,000 deaths due to work-related injuries, and approximately four million workers who suffer non-fatal work-related injuries or illnesses. An estimated 14 million people worked in the United States manufacturing sector in 2010, with 329 deaths due to job injuries, $1.4 million in costs associated with each death, and 127, 140 non-fatal injuries involving days away from work.

In 2008, contact with objects and equipment was the leading cause of workplace death and the leading cause of non-fatal injuries involving days away from work in the United States manufacturing sector. Overexertion is the second leading cause of non-fatal injuries involving days away from work. Although these injuries are widespread, there exists no reliable way to adaptively learn about risk factors and provide warnings in real-time.

SUMMARY

A method for predicting injury risk includes generating state sequences that precede a hazard event based on information regarding a user's state. A cognitive suite of workplace hygiene and injury predictors (WHIP) is generated based on the state sequences using a processor. The cognitive WHIP predicts a degree of risk correlated with each particular user state sequence. An advantageous relationship between the user and one or more socially connected users is determined. An ameliorative action is triggered when a user enters a high-risk state based on the advantageous relationship to the one or more connected users and proximity of the user to one or more other users.

A method for predicting injury risk includes generating state sequences that precede a hazard event based on information regarding a user's state including user biometric information from a device worn by the user and a user's location from one or more workplace monitoring devices. A cognitive suite of workplace hygiene and injury predictors (WHIP) is generated based on the state sequences using a processor and supervised learning. The cognitive WHIP predicts a degree of risk correlated with each particular user state sequence. An advantageous relationship between the user and one or more socially connected users is determined. An ameliorative action is triggered when a user enters a high-risk state based on the advantageous relationship to the one or more connected users and proximity of the user to one or more other users.

A system for predicting injury risk includes a cognitive suite of workplace hygiene and injury predictors (WHIP) module having a processor configured to generate state sequences that precede a hazard event based on information regarding a user's state and to generate a cognitive WHIP based on the state sequences. The cognitive WHIP predicts a degree of risk correlated with each particular user state sequence. A social network module is configured to determine an advantageous relationship between the user and one or more socially connected users. An alert module is configured to trigger an ameliorative action when a user moves into an area of high risk based on the cognitive WHIP.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Embodiments of the present invention use wearable sensors to gather information about workers and how they behave while performing tasks in the workplace. This information is coupled with analytics to provide the basis for optimizing tasks for health and safety. The present embodiments correlate behavioral and wearable physiological measures of employee states in, e.g., a workplace environment, with injury-related events to create a set of predictors of these events that process information streams continually and in real-time.

It is to be understood in advance that, although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Figure 1:
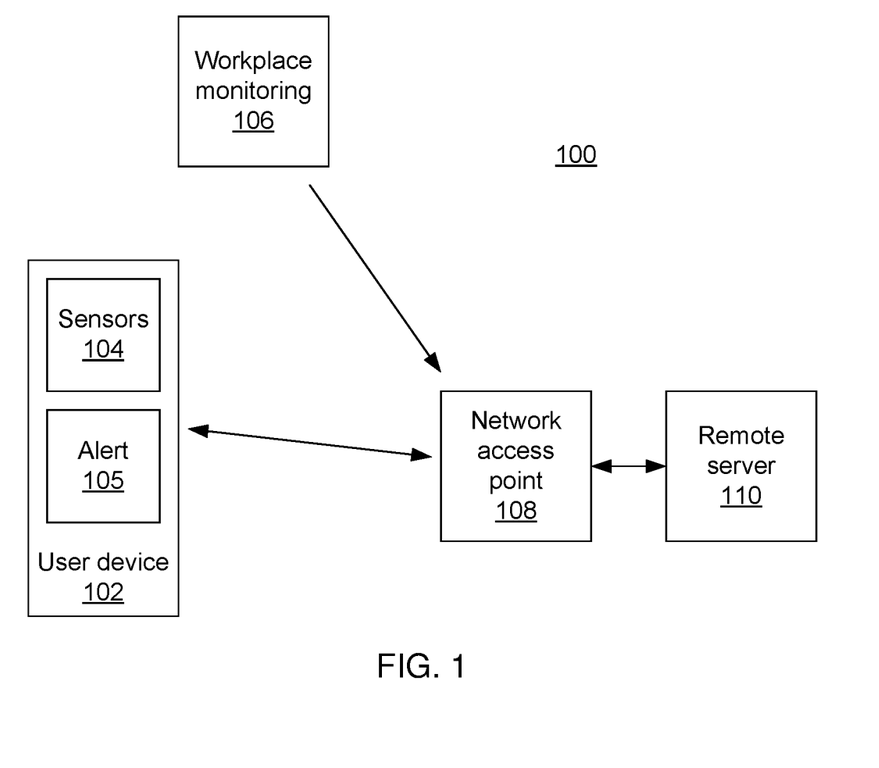
FIG. 1 is a block diagram of a workplace risk management system in accordance with the present principles.

Referring now to FIG. 1, a monitoring and feedback system 100 is shown. A user device 102 is worn by a user or otherwise directly monitors the user's state with one or more sensors 104. In one example, the user device is a wristband equipped with a heart rate sensor and an accelerometer. Other sensors 104 that may be employed include location, time, skin conductivity, moisture, temperature, brainwave, and any other sensor that acquires biometric information about the user.

A user device 102 communicates information collected from the sensors 104 back to a remote server 110 via a network access point 108. It is particularly contemplated that the user device 102 communicates with the network access point 108 via continuous wireless communication, but it is also contemplated that the user device 102 may communicate periodically or at scheduled intervals or via a wired medium. It should naturally be understood that multiple user devices 102 may be employed in a single workplace, for example worn by each worker. Other workplace monitoring sensors 106 may additionally gather data about the user in the workplace and send it to the remote server 110 via the network access point 108. The workplace monitoring sensors 106 may include, for example, video cameras or audio sensors, worker positioning sensors, ambient condition sensors, etc.

The network access point 108 may communicate with the remote server 110 via any appropriate medium, including through the internet. It should be understood that the remote server 110 may be a single, centralized server or may alternatively be a decentralized set of devices. In one specifically contemplated embodiment, the remote server 110 is implemented as a cloud computing solution that includes a large set of distributed computing devices that are provisioned as needed to meet demand.

The remote server 110 performs analytics on the information acquired by the user device 102 and workplace monitoring 106. User states (including, e.g., their physical, cognitive, and emotional state) are determined based on the collected biometric information and the workplace monitoring information and categorized using unsupervised learning. Upon the occurrence of, for example, an industrial hygiene or injury event, the states are further categorized using supervised learning to identify state sequences that precede or do not precede these events. The sequences of user states that predict events (for example, a decreased heart-rate that might indicate drowsiness) are compiled as a cognitive suite of workplace hygiene and injury predictors (abbreviated herein as cognitive WHIPs).

Cognitive and emotional states that are used to form the cognitive WHIPs are defined as functions of measures of a user's total behavior collected over some period of time from at least one personal information collector (including musculoskeletal gestures, speech gestures, eye movements, internal physiological changes, measured by imaging devices, microphones, physiological and kinematic sensors in a high dimensional measurement space) within a lower dimensional feature space. In one exemplary embodiment, certain feature extraction techniques are used for identifying certain cognitive and emotional traits. Specifically, the reduction of a set of behavioral measures over some period of time to a set of feature nodes and vectors, corresponding to the behavioral measures' representations in the lower dimensional feature space, is used to identify the emergence of a certain cognitive and emotional traits over that period of time.

The cognitive WHIP outputs are used to create, for example, a heat map of a factory floor or other workplace environment showing higher and lower degrees of predicted risk of injury or other incidents. The map may be shared with workplace supervisors to use in improving safety conditions. In addition, the remote server 110 may communicate information back to the user device 102 or to other users to provide one or more alerts to the users in the event that the user enters a high-risk state. For example, an alert 105 in the user device 102 may include an audio (e.g., an alarm or spoken warning) or visual (e.g, a flashing light or textual message) indicator. The remote server 110 may also provide its cognitive WHIP outputs to other automation technology in the factory for the purpose of automatically adapting to changing circumstances.

In addition, the remote server 110 may communicate information to users nearby the user device 102. For example, the remote server may determine that there is a user nearby based on workplace monitoring 106, and further determine that that user is in a position to assist with a high-risk situation. As such, upon determining a high risk of industrial hygiene breakdown or injury, the remote server 110 may issue an alert to another user device 102 and provide that user with the ability to, or with an incentive to, assist in preventing or mitigating the incident.

In addition to issuing such alerts based on physical proximity, alerts may be issued based on a user's social network. For example, if an individual is exhibiting high-risk behavior, it may be best to involve someone who knows and is friendly with the user. The remote server 110 can therefore access the user's social network information to determine the best person to respond, even if that person is not physically the closest to the user. This has particular applications when the risk involves mental health, where targeted assistance is needed. In addition, information and incentives can be provided to relevant social groups to promote effective collaboration in minimizing workplace risk. The result of the alerts, information, and incentives may then be measured and used to adjust future actions using a processor and reinforcement learning.

Figure 2:
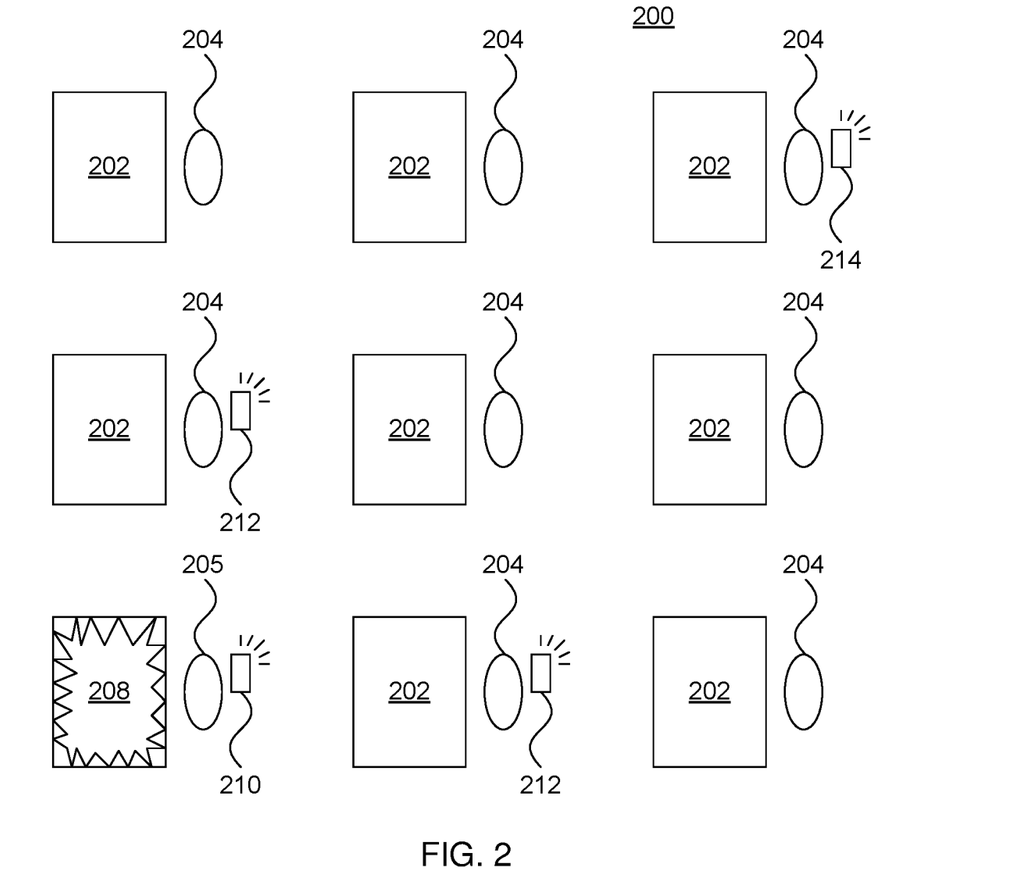
FIG. 2 is a diagram of a workplace environment showing how users are alerted to high-risk states.

Referring now to FIG. 2, an exemplary workplace 200 is shown. The workplace 200 includes, e.g., a number of different regions 202. The regions 202 may represent workstations manned by users 204, discrete pieces of equipment, or any other sensible division of the workplace 200. Notably, regions 202 may be overlapping or non-overlapping and may be characterized by varying types and degrees of risk. Users 204 are distributed through the workplace 200 and may be proximate to one or more regions 202.

In this example, there is a high-risk region 208. This region may be designated as being high risk for any reason, including a set of behaviors by, or sequence of physical or cognitive states of, an at-risk user 205. Each user 204 has a respective user device 102 that may be worn or otherwise kept on the person. When the remote server 110 determines the high risk condition, the device 210 of the user 204 triggering that condition is alerted. In addition, devices 212 of nearby users 204 are alerted with information that may be used to help decrease the risk or to mitigate the damage of an incident. Furthermore, the device 214 of a user 204 who is not physically close, but who has some advantageous relationship to the at-risk user 205, is alerted.

Figure 3:
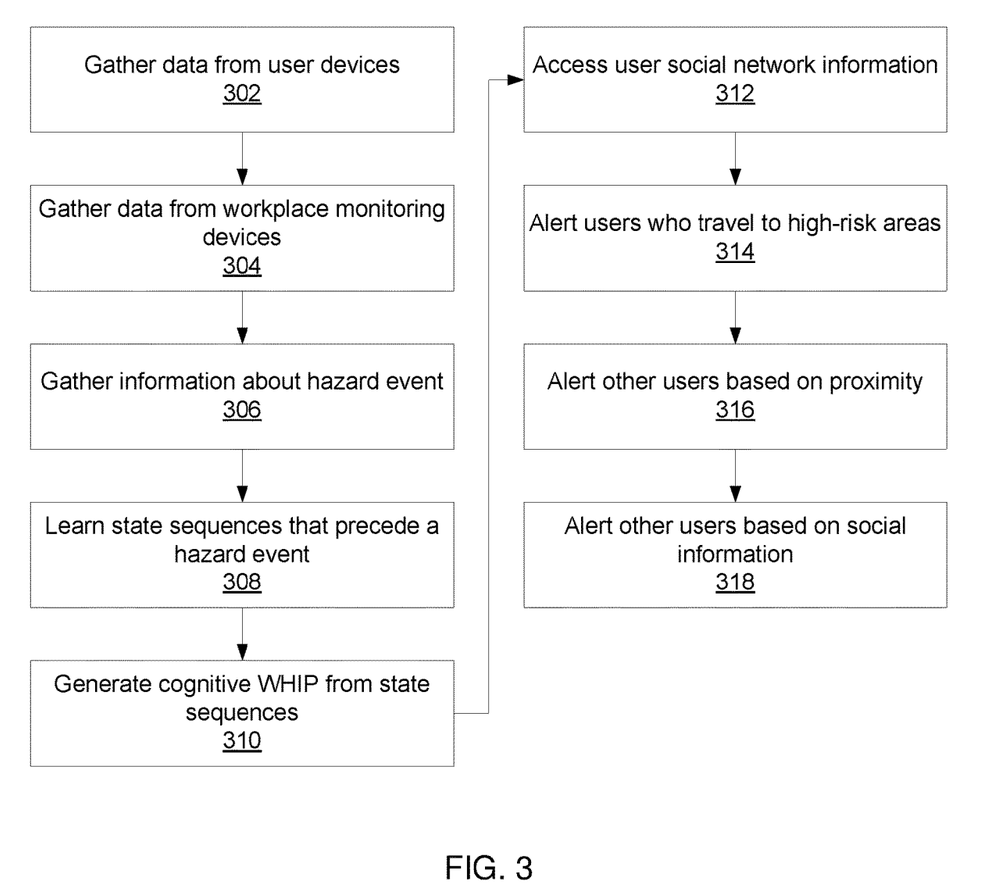
FIG. 3 is a block/flow diagram of a method for managing risk in a workplace in accordance with the present principles.

Referring now to FIG. 3, a method for predicting risk of injury is shown. Block 302 gathers data from sensors 104 on user devices 102 and block 304 gathers data from workplace monitoring sensors 106 via any appropriate medium. Block 306 gathers information about hazard events, including industrial hygiene events and worker injuries. Block 308 then learns state sequences, based on the data gathered about the users, that precede a hazard event. From these sequences, block 310 generates a cognitive WHIP that adaptively predicts whether a given state sequence correlates to a high risk.

Block 312 accesses social network information for the users 204. This information may be publicly accessible information, such as through a social networking website, or may include internal information such as emails to coworkers and other types of social communication. Block 314 then provides alerts to users 205 who move into high-risk areas, including for example providing a visual or auditory alert, providing a textual description of the risk and any ameliorative or mitigating action that can be taken, notifying management of a high-risk situation, and triggering any automatic safety measures that are appropriate. In addition to alerting the at-risk users 205, other users 204 may be alerted based on physical proximity in block 316 and based on the social network information 318. Blocks 314, 316, 318 may also include a processor and reinforcement learning for adjusting future alerts based on outcomes of past alerts.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
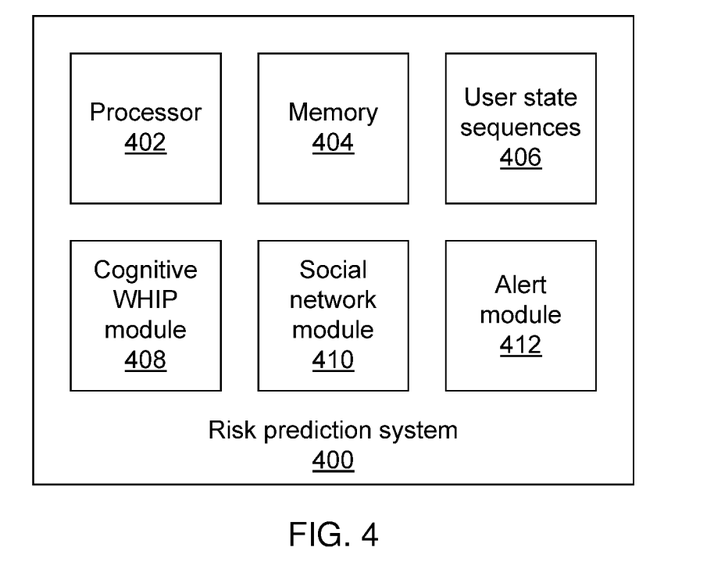
FIG. 4 is a block diagram of a risk prediction system in accordance with the present principles.

Referring now to FIG. 4, a system 400 for predicting risk of injury is shown. The risk prediction system 400 may be implemented as the remote server 110 described above, or may be a distributed cloud system as described below. The system 400 includes a hardware processor 402 and memory 404. The system 400 also includes a set of functional modules that may be implemented, for example, as software stored in memory 404 and executed by the hardware processor 402. Alternatively, the modules may be implemented as one or more discrete hardware components, for example as application specific integrated chips or field programmable gate arrays.

The risk prediction system 400 collects and stores information about the users from user devices 102 and workplace monitoring devices 106 to generate user state sequences. These user state sequences 406 may represent any appropriate set of data relating to the user's actions and physical state within the workplace and are stored in memory 404. A cognitive WHIP module 408 builds cognitive WHIPs based on the user state sequences that lead to hazard events. The cognitive WHIPs generated by cognitive WHIP module 408 predict risk based on a current user state, taking into account, for example, user position, user emotional state, user physical state, user cognitive state, and any other factor which the user state sequences 406 have access to.

A social network module 410 accesses information regarding the users's social connections, in particular by accessing public social network information (e.g., workplace friends) and by accessing internal information (e.g., emails to coworkers), to determine relationships between users 204. An alert module 412 issues alerts that trigger ameliorative action. The ameliorative action may include sending information to user devices 102 and management responsive to a user's operation within a high-risk area 208. The ameliorative action may also include triggering a change in setting of a device or activating a device in the workplace to reduce a degree of risk in the high-risk area. It is particularly contemplated that the alert module 412 may also send alerts to the at-risk user's device 210, to nearby users' devices 212, or to the devices 214 of users who have a particularly advantageous relationship with the at-risk user 205.

Figure 5:
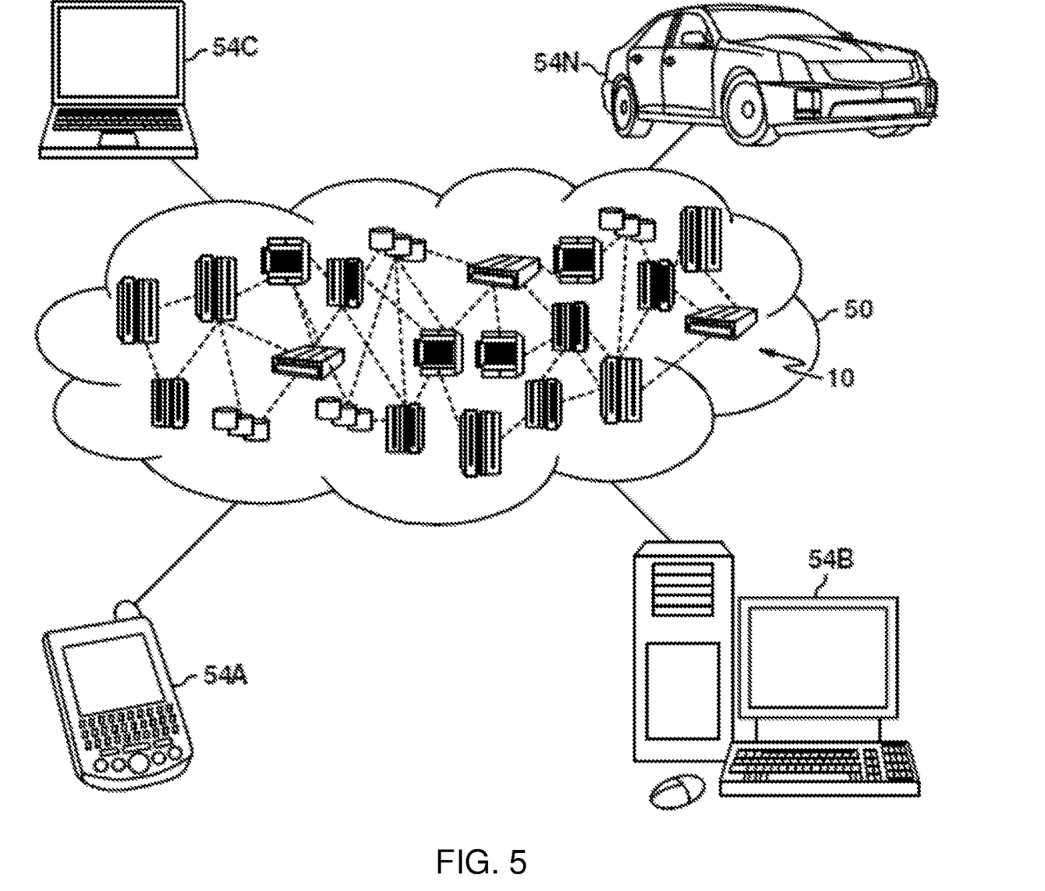
FIG. 5 is a diagram of a cloud computing environment according to the present principles.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 6:
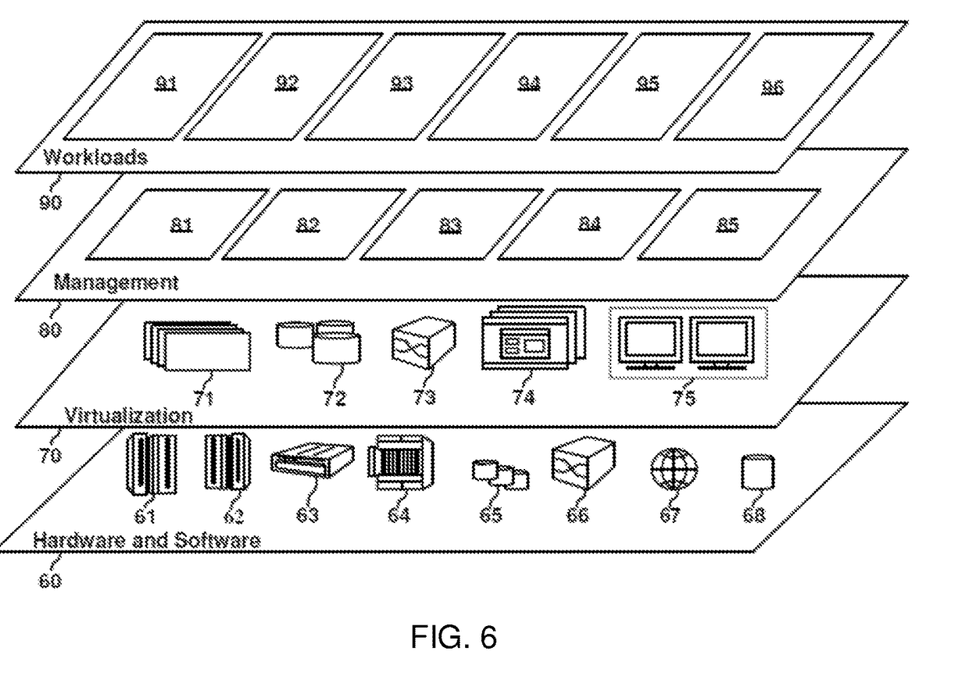
FIG. 6 is a diagram of abstraction model layers according to the present principles.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and risk prediction 96.

Having described preferred embodiments of predictive alerts for individual risk of injury with ameliorative actions (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method for predicting injury risk, comprising:
generating state sequences that precede a hazard event that poses a risk of workplace injury based on information regarding user states by embedding a relatively high-dimensional measurement of the user states in a relatively low-dimensional feature space;
generating a cognitive suite of workplace hygiene and injury predictors (WHIP) based on the state sequences using a processor, wherein the cognitive WHIP predicts a degree of risk of workplace injury correlated with each particular user state sequence;
determining an advantageous relationship between a user and one or more socially connected users;
determining an outcome of a previous ameliorative action;
triggering an ameliorative action responsive to the user entering a high-risk area determined based on the user's state including an indication of user drowsiness, based on the advantageous relationship to the one or more socially connected users, the outcome of the previous ameliorative action, and proximity of the user to one or more other users, including providing an incentive to the one or more socially connected users to reduce the degree of risk; and
triggering an automatic change in a setting of a device in a vicinity of the user in the high-risk state to reduce a degree of risk.

2. The method of claim 1, wherein generating the cognitive WHIP comprises determining state sequences that are related to the hazard event by supervised learning.

3. The method of claim 1, wherein triggering the ameliorative action comprises providing information to the user regarding the user's state.

4. The method of claim 1, wherein triggering the ameliorative action comprises providing information to one or more nearby users, based on proximity, regarding the user's state.

5. The method of claim 1, wherein triggering the ameliorative action comprises providing information to one or more socially connected users, based on the advantageous relationship, regarding the user's state.

6. The method of claim 1, further comprising gathering user state information from a device worn by the user.

7. The method of claim 6, wherein the user state information includes information gathered from one or more skin conductivity sensors, in the device worn by the user.

8. The method of claim 1, further comprising gathering user state information from one or more workplace monitoring devices.

9. A computer readable storage medium comprising a computer readable program for predicting injury risk, wherein the computer readable program when executed on a computer causes the computer to perform the steps of:
generating state sequences that precede a hazard event that poses a risk of workplace injury based on information regarding user states by embedding a relatively high-dimensional measurement of the user's state in a relatively low-dimensional feature space;
generating a cognitive suite of workplace hygiene and injury predictors (WHIP) based on the state sequences using a processor, wherein the cognitive WHIP predicts a degree of risk of workplace injury correlated with each particular user state sequence;
determining an advantageous relationship between a user and one or more socially connected users;
determining an outcome of a previous ameliorative action;
triggering an ameliorative action responsive to the user entering a high-risk area determined based on the user's state including an indication of user drowsiness, based on the advantageous relationship to the one or more socially connected users, the outcome of the previous ameliorative action, and proximity of the user to one or more other users, including providing an incentive to the one or more socially connected users to reduce the degree of risk; and
triggering an automatic change in a setting of a device in a vicinity of the user in the high-risk state to reduce a degree of risk.

10. A system for predicting injury risk, comprising:
a processor;
a memory;
a cognitive suite of workplace hygiene and injury predictors (WHIP) module that is stored in the memory and executed by the processor, configured to generate state sequences that precede a hazard event that poses a risk of workplace injury based on information regarding user states by embedding a relatively high-dimensional measurement of the user states in a relatively low-dimensional feature space and to generate a cognitive WHIP based on the state sequences, wherein the cognitive WHIP predicts a degree of risk of workplace injury correlated with each particular user state sequence;
a social network module that is stored in the memory and executed by the processor, configured to determine an advantageous relationship between a user and one or more socially, connected users; and
an alert module that is stored in the memory and executed by the processor, configured determine an outcome of a previous ameliorative action, to trigger an ameliorative action responsive to the user moving into a high risk area determined based on the user's state$_7$ including an indication of user drowsiness, based on the advantageous relationship to the one or more socially connected users, the outcome of the previous ameliorative action, and proximity of the user to one or more other users, including providing an incentive to the one or more socially connected users to reduce the degree of risk, and further configured to trigger an automatic change in a setting of a device in a vicinity of the user in the high-risk area to reduce a degree of risk.

11. The system of claim 10, wherein the cognitive WHIP module is further configured to determine state sequences that are related to the hazard event by supervised learning.

12. The system of claim 10, wherein the alert module is further configured to provide information to the user regarding the user's state.

13. The system of claim 10, wherein the alert module is further configured to provide information to one or more nearby users, based on proximity, regarding the user's state.

14. The system of claim 10, wherein the alert module is further configured to provide information to the one or more socially connected users, based on the advantageous relationship, regarding the user's state.

15. The system of claim 10, wherein the cognitive WHIP module is further configured to gather the information regarding user states from a device worn by one or more users.

16. The system of claim 15, wherein the user state information comprises biometric information relating to at least one measurable aspect of the user's cognitive state.

17. The system of claim 10, wherein the cognitive WHIP module is further configured to gather the information regarding the user states from one or more workplace monitoring devices.

18. The method of claim 1, wherein triggering the ameliorative action includes selecting a user, from the one or more socially connected users with an advantageous relationship, who is not physically closest to the user.

19. The method of claim 1, further comprising adjusting future ameliorative actions based on results of the ameliorative action using reinforcement learning.

20. The method of claim 1, wherein the relatively high-dimensional measurement of the user's state is represented as a vector in the relatively low-dimensional feature space.

* * * * *